United States Patent [19]
Gabay

[11] Patent Number: 5,854,469
[45] Date of Patent: Dec. 29, 1998

[54] HEATING UNIT FOR THERAPEUTIC INSTRUMENT

[76] Inventor: David Gabay, 92 Parkhurst Rd., Gansevoort, N.Y. 12831

[21] Appl. No.: 673,345

[22] Filed: Jun. 28, 1996

[51] Int. Cl.⁶ ..................................................... H05B 3/70
[52] U.S. Cl. ........................................... 219/521; 219/450
[58] Field of Search ................................... 219/520, 521, 219/524, 532, 533, 534, 535, 450

[56] References Cited

U.S. PATENT DOCUMENTS

| | | |
|---|---|---|
| 1,367,952 | 2/1921 | Emerson . |
| 2,220,043 | 10/1940 | Humphrey et al. ...................... 219/521 |
| 2,843,719 | 7/1958 | Smith et al. . |
| 4,253,013 | 2/1981 | Mabuchi . |
| 4,420,681 | 12/1983 | Arnold .................................... 219/521 |
| 4,896,023 | 1/1990 | Uchiyama . |
| 5,132,518 | 7/1992 | Solacoff . |
| 5,231,266 | 7/1993 | Warren ................................... 219/521 |
| 5,399,840 | 3/1995 | Goeddeke ............................... 219/521 |

*Primary Examiner*—Tu Ba Hoang
*Attorney, Agent, or Firm*—Schmeiser, Olsen & Watts

[57] ABSTRACT

A thermal output device for heating therapeutic ultrasound transducer heads. Typically, a plastic non-conductive housing or case is provided a cutout receptacle which houses a molded tray insert to accommodate insertion therein of various shapes and sizes of ultrasound head transducers. The case is either wall mountable or may safely rest on a horizontal table or shelf. No connection is made either functionally or operationally to the ultrasound unit when it is in operation. The heating element consists in an insulated nichrome wire-wafer type element which is fixed in the receptacle bottom or bed. The element is regulated by an on/off switch and a trimmer component to control heating of the element. Provision is made in the invention to handle various sized and shaped ultrasound transducer instruments. The heating element does not directly contact the patient or the ultrasound head, while it's output is maximized (for safety) at about 5 watts. A thermocouple feedback loop and a temperature display are provided as a higher end option in production of the invention.

7 Claims, 2 Drawing Sheets

HEATING UNIT FOR THERAPEUTIC INSTRUMENT

BACKGROUND OF THE INVENTION

1. Field of the Invention

This invention relates generally to heating/warming devices and, in particular, to a unit useful for warming medical/therapeutic instruments such as stethoscopes, probes, ultrasound heads and similar body-contacting instruments.

2. Description of the Relevant Art

Although the instant invention may be used for warming a variety of body-contacting instruments, the thrust of this description is directed specifically toward the warming of a therapeutic ultrasound (transducer) head in order to provide reasonable patient comfort during use of the instrument. Typically, therapeutic ultrasound is used by physical therapists, chiropractors, athletic trainers and practitioners to apply therapeutic technique, while diagnostic ultrasound is employed by physicians for vascular studies and examination of internal body organs.

A long experienced problem of patient discomfort is encountered during ultrasound administration. Typically, the ultrasound head is at room temperature (68–73 degrees F.), and the human body is, normally, 98.6 degrees. The sudden application of an ultrasound head, some 20–25 degrees cooler than the skin, causes the patient to flinch, pull away or tighten the musculature at contact. This response can increase spasm and tonicity of tight muscles and cause both pain and discomfort for the patient. Seeking to avoid, or at least ameliorate, this problem, I searched the literature and had performed for me a search of the records of the U.S. Patent and Trademark Office.

A relevant disclosure, a U.S. Pat. No. 4,253,013, discloses an electric heating device for warming the shaving head of an electric shaver. The shaver head warmer comprises one or more heating cylinders that are fit closely to the shaving head of an electric shaver. The heating element is made of nichrome wire interposed between mica plates and is positioned between an aluminum base plate and a heat transfer plate. The heat transfer plate is attached to the base of the heating cylinder. The temperature is controlled by a temperature control system having contact springs, one of which is supported by a bimetallic element. The temperature at which the bimetallic element will cause the contacts to move apart is set by means of the temperature control knob. A safety fuse and an indicator lamp are also provided to protect the unit from overheating. There appears to be no provision made for heating razor heads of diverse size or shape.

U.S. Pat. No. 5,132,518 discloses a device for warming medical diagnostic instruments. The device consists in a vented housing having a hinged front access opening, a reflective, flexible metal liner and an electric heat lamp (within the housing), the radiant energy of which is reflected toward the instrument to be heated and which is vertically positioned between the heat source and the access panel. The device is used exclusively to heat stethoscopes and, because of the size and shape, is not readily adapted to the heating of ultrasound heads. Alternatively, this device is realized with a wire type heating element thermal source, but the heat transfer method (convection) remains the same.

A limited number of manufacturers employ an integrated heating device in the ultrasound head itself. These are both expensive and complicated to repair and/or calibrate. A heater malfunction necessitates the complete head replacement or servicing and is likely to incur a major expense. Some practitioners have elected to heat the ultrasound coupling gel before the head is applied to the patient. This practice tends to change viscosity of the gel and does not solve the problem of the cold ultrasound head touching the patient's body.

Far less relevant patents that disclose heating units adapted for specific heating situations include U.S. Pat. Nos. 1,367,952, for heating shoemaking tools, 2,843,719, for heating a bottle, and 4,896,023, a dry and wet heater for heating elongate or tubular items.

3. Incorporation by reference

Because they relate, generically, to the instant invention and, to some extent, disclose art or techniques incorporated in the instant invention, U.S. Pat. Nos. 5,132,518, 4,253,013, 4,896,023, 2,843,719 and 1,367,952 are herein incorporated by reference.

SUMMARY OF THE INVENTION

To my knowledge, a relatively inexpensive, stand-alone heating unit having adaptability to accommodate existing ultrasound heads is not in use in the field. Because the cited problem yet exists, there is a need for a heating unit specifically for therapeutic ultrasound heads. My invention is such a stand-alone unit in which the ultrasound head is cradled in a head warming device. As the reader will appreciate, any existing ultrasound unit may be readily prepared for increased patient comfort through use of my invention.

A nonconductor housing or case, preferably made of plastic, includes a cutout receptacle which will receive an ultrasound head transducer. Use of a molded insert in the cutout receptacle allows the user to heat various shapes and sizes of ultrasound heads that currently exist. The housing may be wall mounted or rest safely on a table or shelf as a stand-alone unit. Heat transfer to the ultrasound head is generally by way of conduction, but the invention is not connected by function nor operation to the ultrasound head/unit. The heating element is an insulated nichrome wire wafer type element which attaches to the receptacle bed, is driven by conventional heating circuitry and controlled by conventional switching and trimming devices. An adjustable fork or col is positioned apart from the receptacle allowing adjustability to various sized and shaped handles found on the different ultrasound transducers.

The heating element does not directly contact the patient nor the ultrasound head. The power source is a 110 volt external step-down transformer with an output of approximately 12 volts at approximately 5 watts. Included in the circuitry, although not required for basic functioning, is a thermocouple feedback loop and temperature display.

In operation, the user places the ultrasound head into the receptacle (using an insert such as silicone spacers or an annular tray) so that contact is made with the bottom of the receptacle cup and the head which, regardless of size, fits within the receptacle. The handle of the transducer is rested on the fork or col which is adjusted vertically so as to allow comfortable grasping of the handle. The unit is switched on and the temperature adjustment knob regulated to acquire the desired temperature. Use of the invention in its less expensive mode, that is, having no temperature indicator, is not limited because the special power source and control circuitry combined with the special posturing of the head within the receptacle limits the amount of thermal energy that can be transferred to the ultrasound head. Thus, were the user to be inattentive, there is little or no likelihood of excessively heating the ultrasound head.

DETAILED DESCRIPTION OF THE PREFERRED EMBODIMENT

Figure 1:
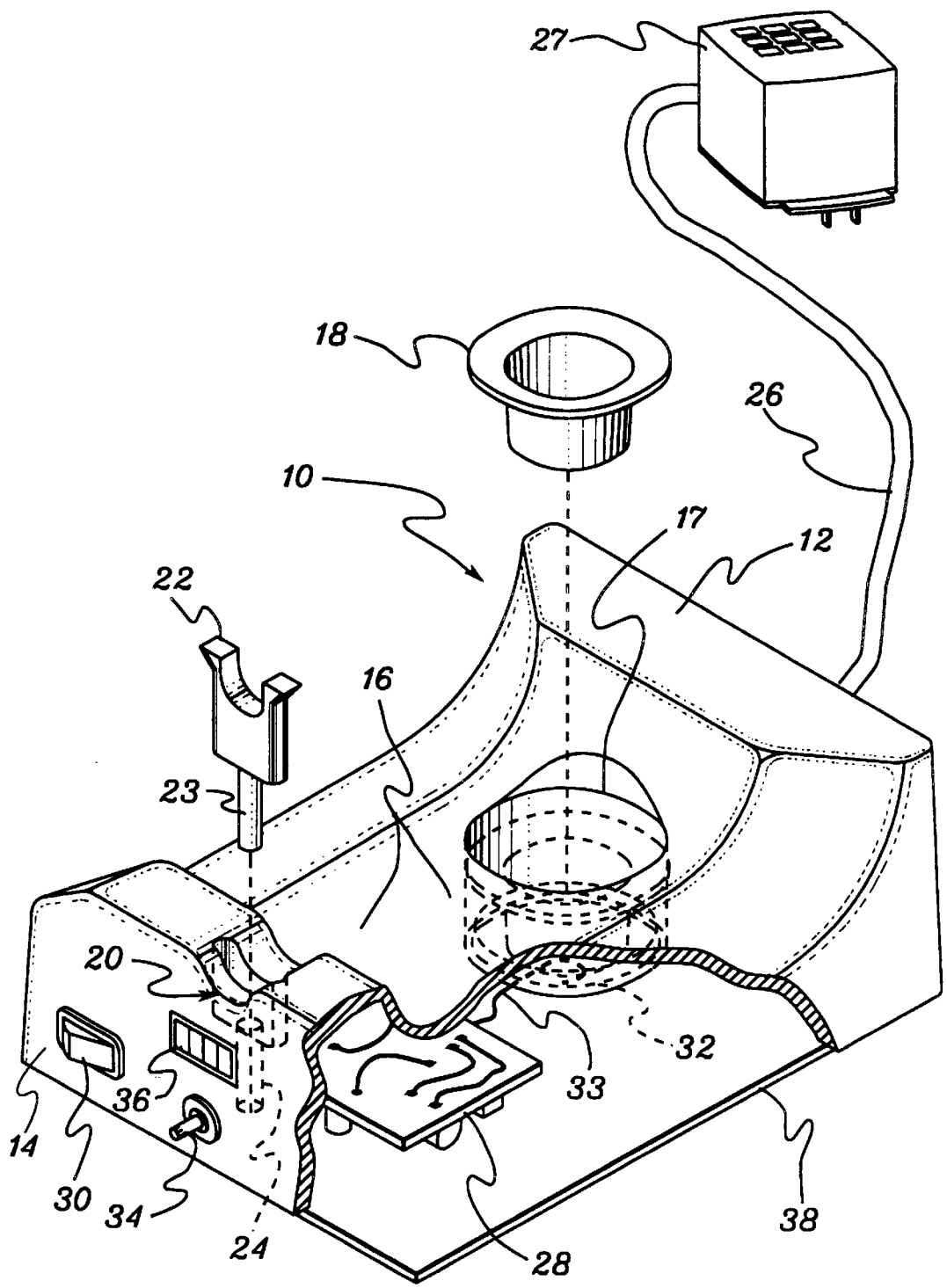
FIG. 1 is an illustration of the invention in partial cutaway.

Referring particularly to FIG. 1, a device made in accordance with the teaching of my invention is depicted as a case 10 or housing, preferably molded of high density heat resistant plastic, that is characterized as essentially oblong in nature and having an elevated rear end 12 and an opposing elevated front end 14. Between the elevated ends there is situated a ridge 16 giving the overall resemblance to the invention case 10 of a saddle. Located on the ridge center line, but disposed slightly toward the rear end 12 of the case is a circular depression, called a receptacle 17. The single receptacle is essentially cup shaped and possesses a defined base area. The receptacle 17 receives a single transducer head. A drop-in tray or holder 18 of annular geometry is provided for insertion into the receptacle 17. Other separators (not shown) such as silicone fingers are also used to perform a spacing function within the receptacle. Located center-top on the elevated front end 14 is a semi-circular groove known as the fixed col 20. A cut-out and throughhole 24 is provided central of the fixed col 20 in order to receive therein the shaft 23 portion of adjustable col 22. Both the fixed and adjustable cols 20, 22 are provided to receive therein the various sized and shaped handles of existing ultrasound head instruments. It may be realized that the aforementioned tray 18 or silicone finger (inserts) are provided in order to accommodate the various sizes of ultrasound heads. At one end of the case 10, here the rear end 12, power supply means are provided and delivered through power cord 26. At either of the ends, here the front end 14, three devices are depicted: an on/off switch 30; a temperature adjustment knob 34; and, a temperature readout device 36 which may be of the analogue or digital type. A bottom cover 38 is also provided in the model of the invention shown. Optional to the power circuitry to be addressed hereinafter, is the step-down transformer 27 that I have selected in order to easily maximize the available power output of my invention. Maximization of output power, predicated on the maximum threshold of input power grants an inherent safety feature to my invention.

The above description concludes the detail of major externalities of my invention. Referring to the cut away portion of FIG. 1, there is depicted a circuit board 28, a planar heater wafer assembly 32 and a nichrome heating wire 33.

Figure 2:
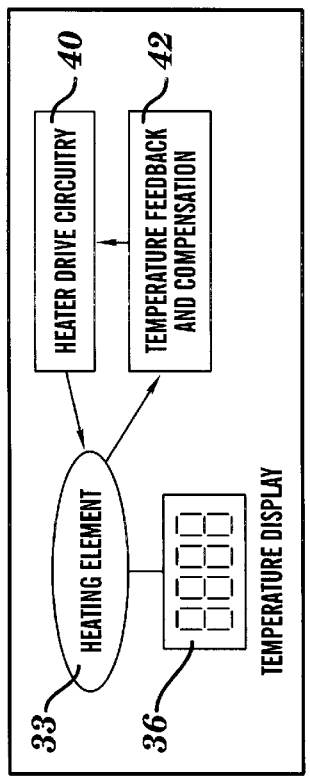
FIG. 2 is a block diagram of the functional aspects of the invention.

FIG. 2 is a block diagram of the circuitry and optional instrumentation of the invention. Heater drive circuitry 40 is used to provide electrical power to the heating element 33. Temperature feedback and compensation circuitry 42 assures proper control over the output of the heater drive circuit 40. In high end versions of my inventions, a temperature display instrument 36, of either digital or analogue nature, may be used.

Figure 3:
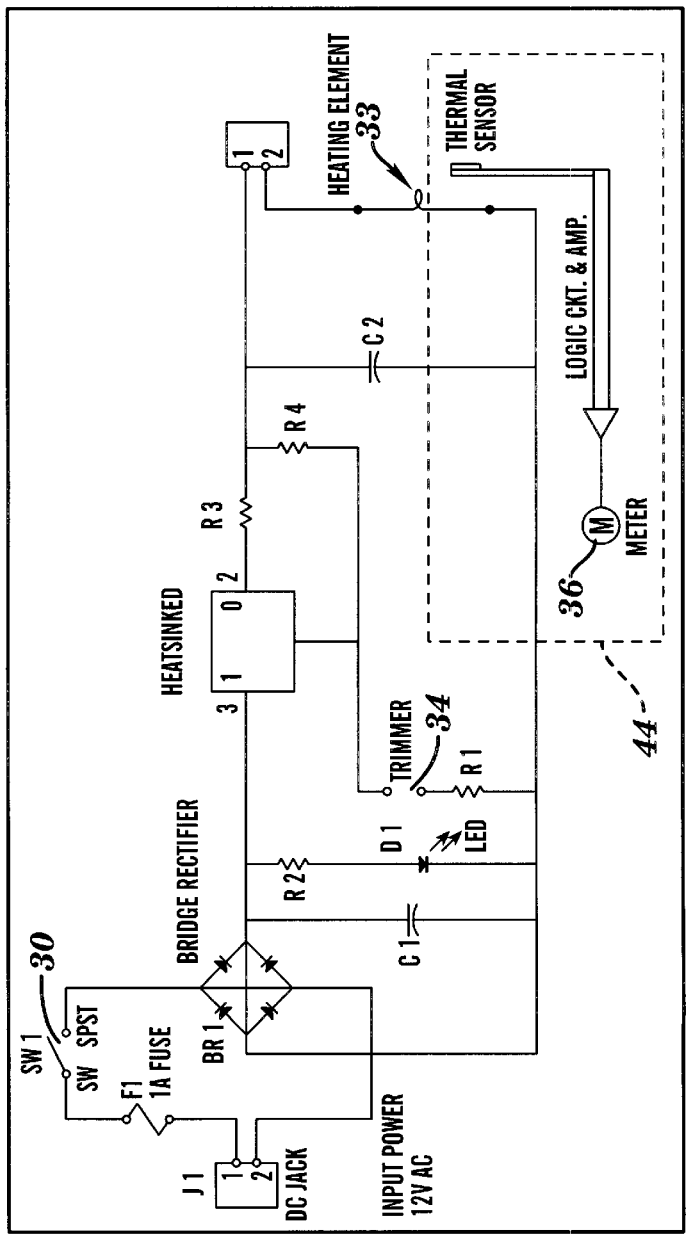
FIG. 3 is an electrical schematic of the principal circuitry.

The schematic diagram of FIG. 3 relates the nominal circuitry which I have employed to provide the desired power requirements of my invention. The circuitry is conventional and notation is made specifically to the on/off switch 30, temperature adjustment knob (trimmer) 34 and the temperature readout display 36. The optional circuit, that used for the temperature display 36, is denoted by the dashed lines 44 and may be realized by addition of a baby board (not shown) or included on the existing circuit board 28.

Having disclosed all functional and operative aspects of my invention, I have provided to the field a much needed device to solve the problem herein defined. Such is commended to the practitioners in the field consistent with the hereinafter appended claims.

What is claimed is:

1. A stand-alone thermal unit for warming a portion of a body-contacting instrument comprising, in combination:

a non-conductive case having a saddle shape defined by elevated front and rear ends with a lower ridge therebetween, a circular depression disposed proximately central of said ridge and a manually height-adjustable col member disposed in an uppermost portion of at least one of said ends; and an electrical heating element comprising a nichrome filament sandwiched between two mica wafers and disposed in said depression, said heating element connected to a power control circuit contained within said case and which is operable by a manual control means included therein.

2. The unit of claim 1 wherein said circular depression is a cup shaped receptacle.

3. The unit of claim 2 further comprising an insert means that is insertable in said receptacle for adapting it to hold said portion of said instrument having a smaller or diverse shape.

4. The unit of claim 1 wherein said manual control means comprises on/off switch means and a temperature control means.

5. The unit of claim 4 wherein said power control circuit further comprises a thermocouple feedback loop and a temperature display.

6. Apparatus for warming a transducer head of an ultrasound comprising:

a case containing electrical power control circuitry including a planar heating element, temperature feedback circuitry and compensation circuitry, wherein said case consists of one receptacle of receiving a holder therein, said heating element being positioned within said receptacle and separately adjacent to said holder.

7. A method for using a heater for warming a transducer head of an ultrasound comprising:

providing a housing having electrical power control circuitry including a heating element, temperature feedback circuitry, compensation circuitry, and a single depression;

providing a holder for receiving said transducer head in which said heating element is separated from said holder;

placing said holder in said depression;

heating said transducer head in said depression; and removing said transducer head, after heating for use.

* * * * *